US011963959B2

(12) United States Patent
Bohmann et al.

(10) Patent No.: US 11,963,959 B2
(45) Date of Patent: Apr. 23, 2024

(54) INHIBITORS FOR CORONAVIRUS

(71) Applicants: Southwest Research Institute, San Antonio, TX (US); The Government of The United States, as represented by The Secretary of the Army, Fort Detrick, MD (US); The Henry M. Jackson Foundation for the Advancement of Military Medicine, Inc., Bethesda, MD (US)

(72) Inventors: Jonathan A. Bohmann, San Antonio, TX (US); Nadean M. Gutierrez, Devine, TX (US); Joseph A. Mcdonough, Helotes, TX (US); Robert Francis Campbell, Edgemere, MD (US); Michael Gordon Joyce, Silver Spring, MD (US); Rekha Panchal, Fort Detrick, MD (US); Rajeshwer Sankhala, Bethesda, MD (US); Allen Duplantier, Stafford, VA (US)

(73) Assignees: Southwest Research Institute, San Antonio, TX (US); The Government of the United States, as represented by The Secretary of the Army, Fort Detrick, MD (US); The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 17/819,524

(22) Filed: Aug. 12, 2022

(65) Prior Publication Data

US 2023/0065024 A1 Mar. 2, 2023

Related U.S. Application Data

(60) Provisional application No. 63/260,341, filed on Aug. 17, 2021.

(51) Int. Cl.
*A61K 31/517* (2006.01)
*A61K 31/427* (2006.01)
*A61P 31/14* (2006.01)

(52) U.S. Cl.
CPC .......... *A61K 31/517* (2013.01); *A61K 31/427* (2013.01); *A61P 31/14* (2018.01)

(58) Field of Classification Search
CPC ...... A61K 31/517; A61K 31/427; A61P 31/14
See application file for complete search history.

(56) References Cited

U.S. PATENT DOCUMENTS

2019/0374544 A1  12/2019  Bantia et al.

FOREIGN PATENT DOCUMENTS

WO         2021/035045        2/2021

OTHER PUBLICATIONS

PubChem CID 85934146 (Year: 2014).*
PubChem CID 85933570 (Year: 2014).*
International Search Report and Written Opinion from corresponding PCT Appln. No. PCT/US2022/074929, dated Dec. 15, 2022.
Invitation to Pay Additional Fees from corresponding PCT Appln. No. PCT/US2022/074929, dated Sep. 30, 2022.
"SID 365669431", PubChem, downloaded Sep. 27, 2022, concise explanation of relevancy can be found in the Invitation to Pay Additional Fees submitted herewith.

* cited by examiner

*Primary Examiner* — Shengjun Wang
(74) *Attorney, Agent, or Firm* — Grossman, Tucker, Perreault & Pfleger PLLC

(57) ABSTRACT

Inhibitors against SARS-COV-1, SARS-CoV-2 (Covid-19), MERS-CoV, and variants within each, including methods of treating a subject suffering from such respiratory disease.

10 Claims, 17 Drawing Sheets

INHIBITORS FOR CORONAVIRUS

STATEMENT REGARDING FEDERALLY SPONSORED RESEARCH OR DEVELOPMENT

This invention was made with government support under W81XWH-18-2-0040 awarded by the United States Army Medical Research and Development Command. The government has certain rights in the invention.

FIELD

The present invention is directed at inhibitors against SARS-COV-1, SARS-CoV-2 (Covid-19), MERS-CoV, and variants within each, including methods of treating a subject suffering from such respiratory disease.

BACKGROUND

Coronavirus disease-19 (COVID-19) has led to a global pandemic. COVID-19 was reportedly first identified in Wuhan (Hubei Province, China) at the end of 2019 and later, the International Committee on Taxonomy of Viruses (ITVC) named it SARS-CoV-2 due to its similarity to SARS-CoV.

SARS-CoV-2 is known to encode various structural and nonstructural proteins. The proteins then facilitate the ability of the virus to enter and replicate inside the host. The non-structural protein includes 3-chymotrypsin-like protease ($3CL^{pro}$) also known as the main protease $M^{pro}$ has therefore been identified as a potential target for drug development. Inhibition of $M^{pro}$ would prevent the virus from replication and therefor amount to a potential anticoronaviral strategy.

Accordingly, the present invention presents new drug compositions and methods of treating a subject suffering from COVID-19. The drug composition preferably target the COVID-19 virus main protease $M^{pro}$ and which is efficacious against multiple COV species, such as SARS-COV-1 and MERS-CoV and variants within each.

DETAILED DESCRIPTION

Figure 1:
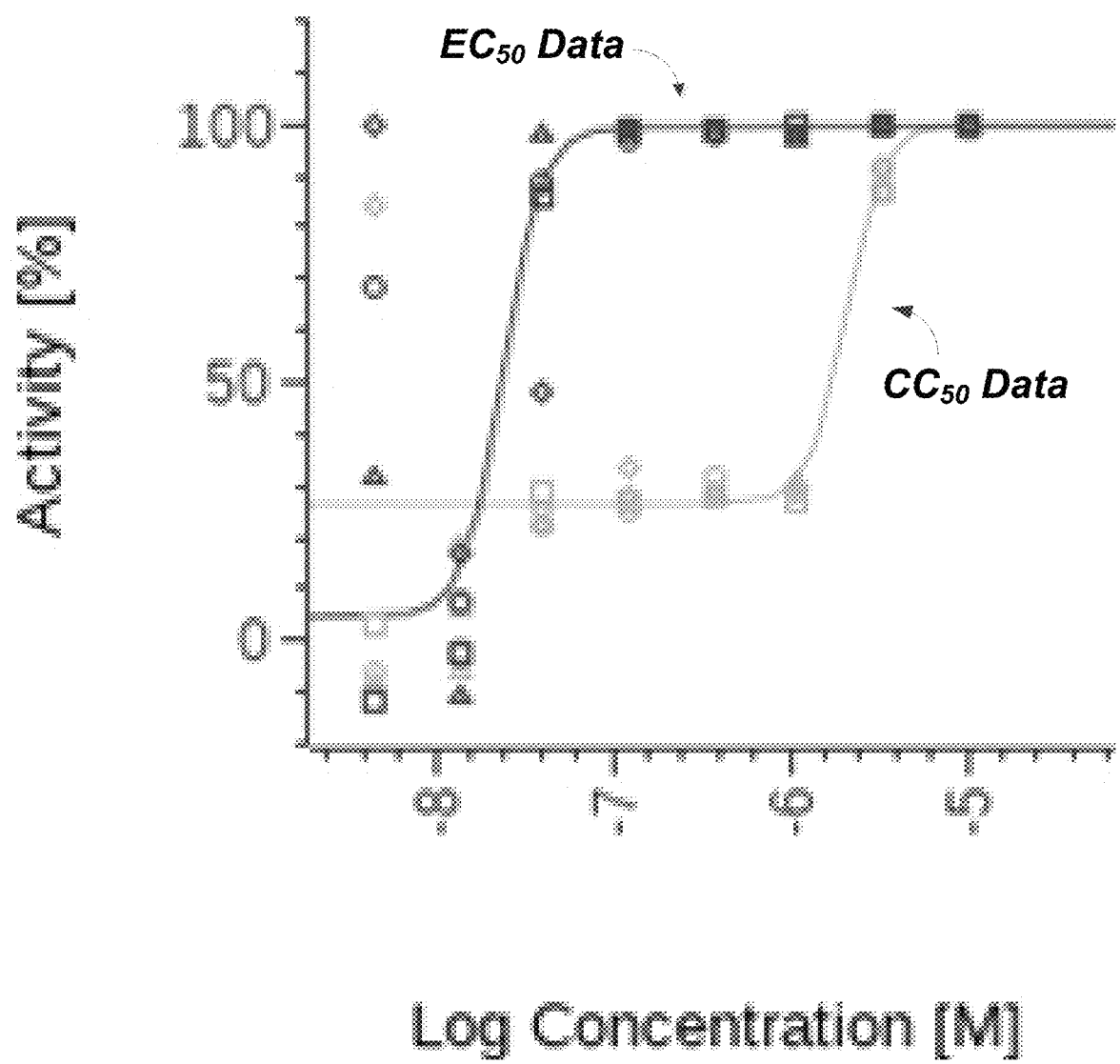
FIG. 1. Dose response curve for Compound 1: 7-(2-(trifluoromethyl)benzyl)-7H-pyrrolo[3,2-f]quinazoline-1,3-diamine.
Figure 2:
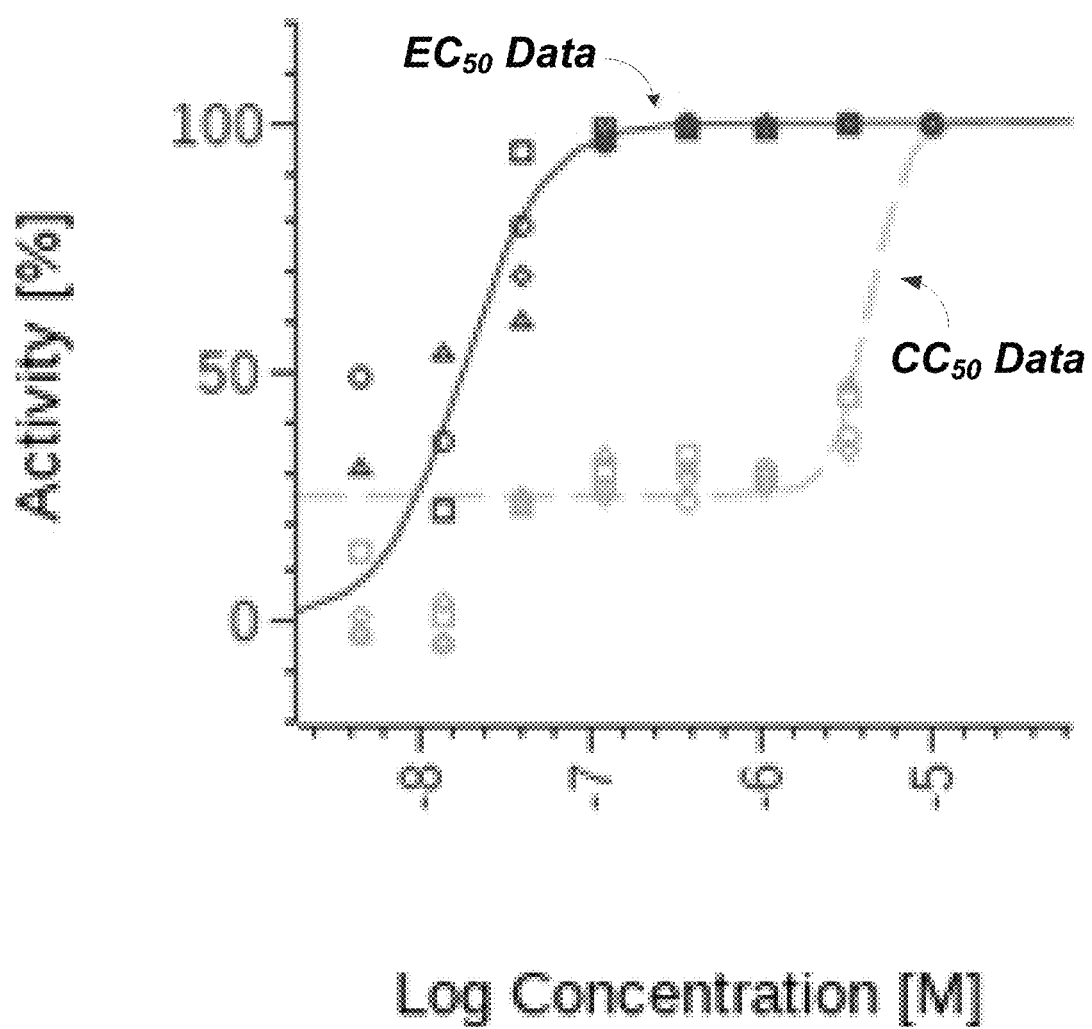
FIG. 2. Dose response curve for Compound 2: 7-(2-methylbenzyl)-7H-pyrrolo[3,2-f]quinazoline-1,3-diamine.
Figure 3:
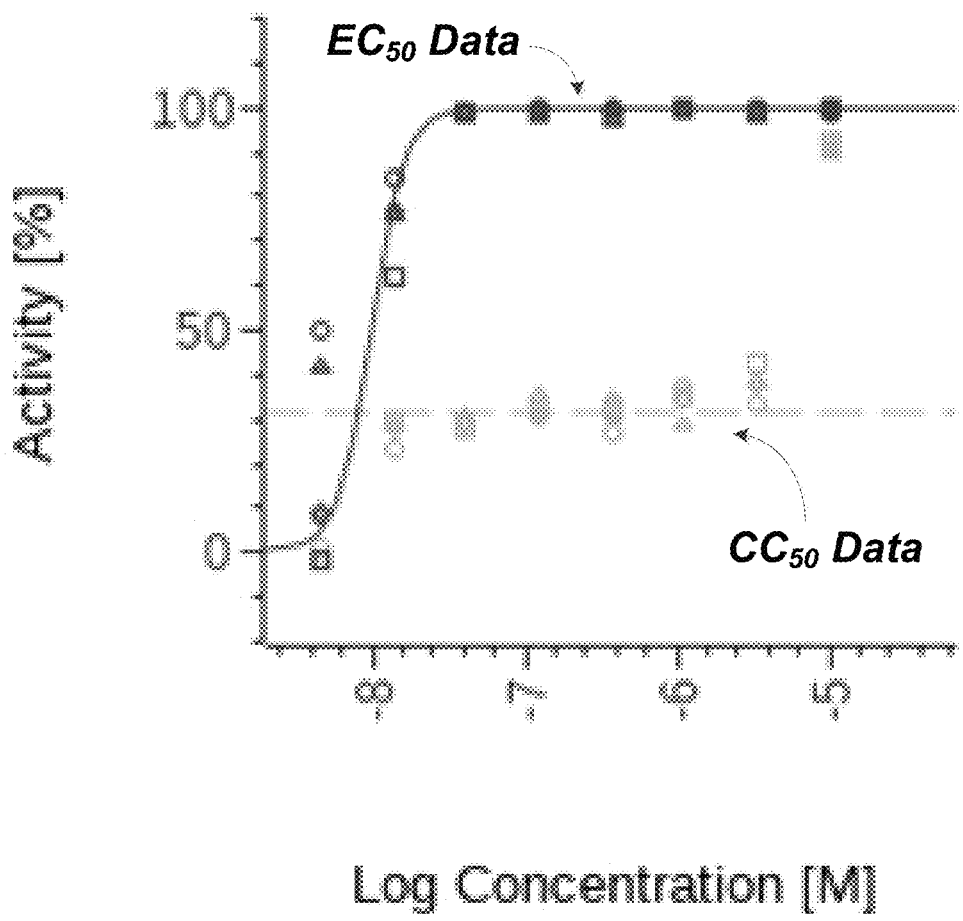
FIG. 3. Dose response curve for Compound 3: 4-((1,3-diamino-8-methyl-7H-pyrrolo[3,2-f]quinazolin-7-yl)methyl)benzonitrile.
Figure 4:
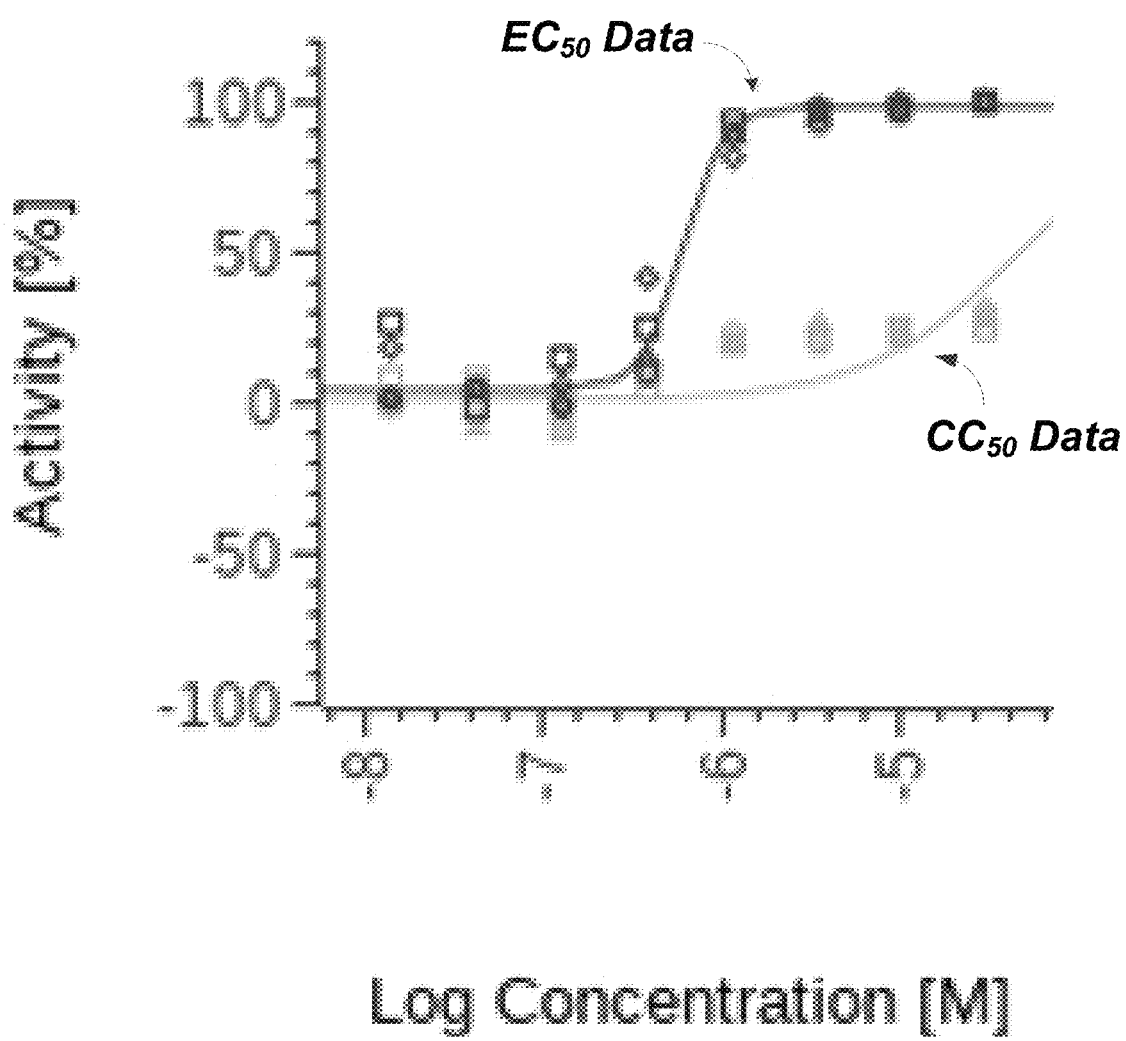
FIG. 4. Dose response curve for Compound 4: 7-allyl-7H-pyrrolo[3,2-f]quinazoline-1,3-diamine.

Compositions are methods of treating a subject suffering from SARS-COV-1, SARS-CoV-2 (Covid-19) and MERS-CoV, and variants within each, are provided. The drug compositions herein may preferably target a conserved binding site. Reference to a subject, individual, host or patient herein are interchangeable and refer to any mammalian subject for which diagnosis, treatment or therapy is desired, particularly humans. Treatment may be any treatment of a disease in a mammal and includes preventing the associated respiratory disease from occurring, inhibiting the disease, arresting its development, or relieving or causing regression of the disease.

$M^{pro}$ In Vitro Screening Protocol

As an initial matter, to identify new potential inhibitors for the main protease of SARS-Cov-2, screening of the drugs identified herein for antiviral activity was conducted. Specifically, primary screening of small molecules was performed by testing the compounds at a single final concentration of 10 μM in two independent replicate plates. Compounds that showed >50% infection inhibition and <20% loss in cell number in both replicated plates were considered as hits. To determine potency and selectivity index of identified hits, compounds were tested in 8-point dose response with a 3-fold step dilution at concentration ranging from 30-0.01 μM and four replicates. N-hydroxy cytidine (NHC), an antiviral with known anti SARS-CoV-2 activity, was used as a reference inhibitor.

All infections with virulent strains were performed in a BSL-3 laboratory in accordance with CDC and US Army safety regulations. To identify small molecule inhibitors of SARS-CoV-2, VeroE6 cells (ATCC CRL-1586) were seeded at a density of 4000 cells/well in a 384 well imaging plates (Aurora Microplates, ABE2-31101A). Next day cells were pre-treated with the compound for two hours and then infected with SARS-CoV-2 (USA-WA1/2020) at a multiplicity of infection (MOI) of 0.01. After 32 hours following infection, cells were fixed in 10% formalin. To detect the viral antigen, immunofluorescence staining was performed wherein formalin fixed cells were washed three times with Phosphate buffered saline (PBS) and then incubated at room temperature (RT) with 50 μl of a combination cell permeabilization and blocking buffer (3% BSA, 0.1% Triton X-100 in PBS). After 1 hour, blocking buffer was replaced with 50 μl primary antibody solution (SARS-CoV/SARS-CoV-2 Nucleocapsid Rabbit Mab, Sino Biological, Cat 40143-R001) diluted 1:1000 in PBS and allowed to bind for 1 hour at RT. After two washes with 50 μl PBS, cells were stained for 30 minutes with 1:500 dilution of Alexa 488 anti-rabbit IgG (Invitrogen A11031). After 30 minutes, cells were washed three times with PBS. In the final step, PBS was replaced with 50 μl per well of 1:10000 Hoechst nuclear dye (Invitrogen H3570) and 5 mg/ml HCS Cellmask Deep Red (Invitrogen H32721), a cytoplasmic stain, all diluted with PBS.

To quantitate viral infection, images were acquired using a Perkin Elmer Opera quad-excitation confocal microscope (model 5025) using a 10× air objective. The nuclei, viral nucleoprotein, and cytoplasm were detected using the 405, 488, and 640 nm channels, respectively. Virus-positive cells were identified by presence of 488 excitation signal within the boundary denoted by cytoplasmic mask. Intensity cutoffs were determined by the intensity of background fluorescence in uninfected control wells, and were normalized for each separate experiment. The robustness of the assay was determined by calculating the Z' value on a per plate basis (Ji-Hu Zhang J, Thomas D. Y. Chung and Kevin R. Oldenburg, *A Simple Statistical Parameter for Use in Evaluation and Validation of High Throughput Screening Assays*, J. of Biomolecular Screening, 4:67, 1999) and using the following formula:

$$(Z'=(1-(3 \times STDEV \text{ of Signal}_{max} \text{ (neutral/infection only control)} + 3 \times STDEV \text{ Signal}_{min}(\text{inhibitor/no infection control}))/ABS(\text{mean Signal}_{max} - \text{mean of Signal}_{min})).$$

Plates that have Z'>0.5 were considered for data analysis. To determine percent of viral infection inhibition and cytotoxicity in presence of compound, the Acapella generated cell data is imported to Spotfire (visual analysis statistical software, Perkin Elmer Inc., MA). Compounds that exhibited greater than 50% inhibition of SARS-CoV-2 infection relative to infected control (infected and DMSO treated) wells and those that did not reduce the number of cells more than 20% relative to the infected control were considered as "Hits". The hit compounds were then selected for dose-response assays.

To determine the potency ($EC_{50}$, $EC_{90}$), cytotoxicity ($CC_{50}$) and selectivity index (SI) of the compounds, dose response curve analysis was performed using GeneData software applying Levenberg-Marquardt algorithm (LMA) for curve-fitting strategy. Fitting strategy is considered acceptable if $R^2>0.8$.

From the above, the top candidates belonging to the family of pyrroloquinazolines were identified as inhibitors of SARS-COV-1, SARS-CoV-2 (Covid-19) and MERS-CoV, and variants within each. These pyyroloquinazolines or pharmaceutically acceptable salts thereof are identified in Formula I below:

wherein $X_1$ and $X_2$ are H, or when $X_1$ and $X_2$ are joined together by a single bond, $X_1$ and $X_2$ are $CH_2$, or when $X_1$ and $X_2$ are joined together by a double bond, $X_1$ and $X_2$ are independently CH or N;

each Y is independently C or N;

Z is C=O, $SO_2$, $CH_2$, $CH_2CH_2$ or a bond;

$R_1$ is $C_1$-$C_{10}$ alkyl, $C_1$-$C_{10}$ alkenyl, cycloalkyl, cycloalkenyl, aryl, heteroaryl, heterocyclyl, wherein each $R_1$ is optionally independently substituted with one to three of Cl, Br, F, hydroxy, alkyl, cycloalkyl, alkoxy, cyano, ethynyl, amino, alkylamino, dialkylamino, acylamino, acyl, nitro or trifluoromethyl;

$R_2$ and $R_3$ are independently a pair of electrons when the Y to which they are connected is N, and are independently H, alkyl, alkenyl or trifluoroalkyl when the Y to which they are connected is C; and R2 and R3 may be taken together to form a 6-membered ring; and $R_4$ and $R_5$ are independently amino groups.

The present invention therefore stands directed at a method of treating severe acute respiratory syndrome coronavirus (SARS-COV-1, SARS-CoV-2 (Covid-19) and middle east respiratory syndrome coronavirus (MERS-CoV), and variants within each, in a mammalian subject in need therefore, which targets (interacts with) the virus main protease $M^{pro}$. The method comprises administering to the subject the compounds of Formula I, or a pharmaceutically acceptable salt thereof, optionally in a pharmaceutically acceptable carrier. The pharmaceutically acceptable carrier may comprise a dosage form suitable for oral administration, such as in a solution or suspension. The dosage form may be in a solid dosage form such as a tablet, capsule or gelcap. The pharmaceutically acceptable carrier may also include a dosage suitable for intravenous delivery.

The administration is contemplated to provide a reduction in the subject's viral load (which can be evaluated via PCR), an improvement in one or more of the subjects' viral infection symptoms (e.g. fever, decreased oxygen saturation, shortness of breath, difficulty breathing, fatigue, muscle aches, body aches, chest pain or pressure, headache, loss of taste, loss of smell, sore throat, congestion, nausea, vomiting, diarrhea, confusion, cough or rash) and/or clinical status. Clinical status may be evaluated utilizing the WHO Ordinal Scale for Clinical Improvement.

Preferably, the antiviral drugs in Formula I herein comprise:

1. Compound 1: 7-(2-(trifluoromethyl)benzyl)-7H-pyrrolo[3,2-f]quinazoline-1,3-diamine having the following general structure:

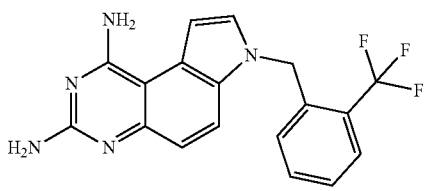 [SMILES: Nc1nc(N)c2c(ccc3c2ccn3Cc2ccccc2C(F)(F)F)n1]

2. Compound 2: 7-(2-methylbenzyl)-7H-pyrrolo[3,2-f]quinazoline-1,3-diamine having the following general structure:

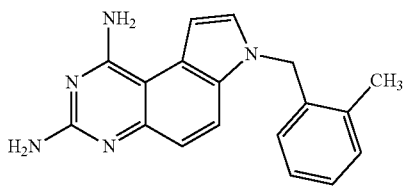 [SMILES: Cc1ccccc1Cn1ccc2c3c(N)nc(N)nc3ccc21]

3. Compound 3: 4-((1,3-diamino-8-methyl-7H-pyrrolo[3,2-f]quinazolin-7-yl)methyl)benzonitrile having the following general structure:

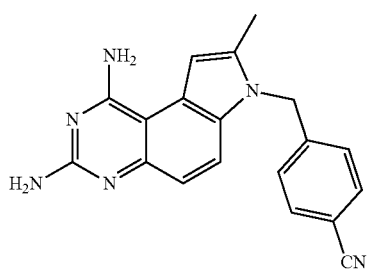 [SMILES: Cc1cc2c3c(N)nc(N)nc3ccc2n1Cc1ccc(C#N)cc1]

4. Compound 4: 7-allyl-7H-pyrrolo[3,2-f]quinazoline-1,3-diamine having the following general structure:

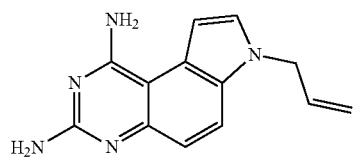 [SMILES: C=CCn1ccc2c3c(N)nc(N)nc3ccc21]

Table 1 below provides data on potency ($EC_{50}$, $EC_{90}$), cytotoxicity ($CC_{50}$) and SI (selectivity index=$CC_{50}/EC_{50}$) for the above referenced compounds against the SARS-CoV-2 strain. $EC_{50}$ is reference to the dose that provides a half-maximal response. $EC_{90}$ is reference to the dose that provides a 90% maximal response. $CC_{50}$ is the concentration required for reduction of cell viability by 50%. The dose response curves for Compounds 1-4 are provided in FIGS. 1-4, respectively.

TABLE 1

| Compound | $EC_{50}$ (µM) | $EC_{90}$ (µM) | $CC_{50}$ (µM) | SI |
|---|---|---|---|---|
| *1 | 0.03 ± 0.01 | 0.07 ± 0.03 | 2.0 ± 0.25 | 66.8 |
| *2 | 0.02 ± 0.004 | 0.032 ± 0.05 | 4.94 ± 0.55 | 245 |
| *3 | 0.013 ± 0.005 | 0.03 ± 0.02 | 6.41 ± 0.70 | 477.3 |
| *4 | 0.47 ± 0.21 | 0.85 ± 0.46 | >30 | >63.8 |

*Represents two biological replicates and 8 technical replicates

In addition, from the above screening protocol, the top candidates belonging to the family of thiazoles were identified as inhibitors against the main protease ($M^{pro}$) of SARS-COV-1, SARS-CoV-2 (Covid-19) and MERS-CoV, and variants within each. These are identified in Formula II below:

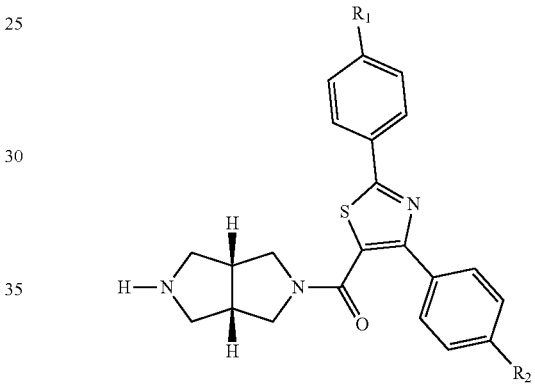

In the above formula, $R_1$ and $R_2$ are independently H or Cl. In addition, it is contemplated that the thiazoles above include a pharmaceutically acceptable salts thereof and may optionally be in a pharmaceutically acceptable carrier.

Preferably, the antiviral drugs in Formula II herein comprise:

5. Compound 5: (2,4-diphenylthiazol-5-yl)((3aR,6aS)-hexahydropyrrolo[3,4-c]pyrrol-2(1H)-yl)methanone, having the following general structure:

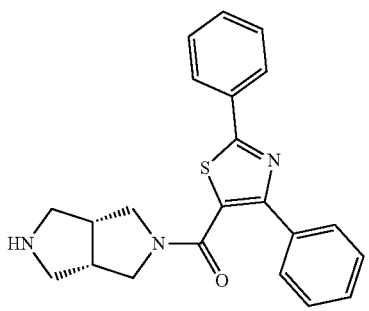 [SMILES: O=C(c1sc(-c2ccccc2)nc1-c1ccccc1)N1C[C@H]2CNC[C@H]2C1]

6. Compound 6: (4-(4-chlorophenyl)-2-phenylthiazol-5-yl)((3aR,6aS)-hexahydropyrrolo[3,4-c]pyrrol-2(1H)-yl)methanone, having the following general structure:

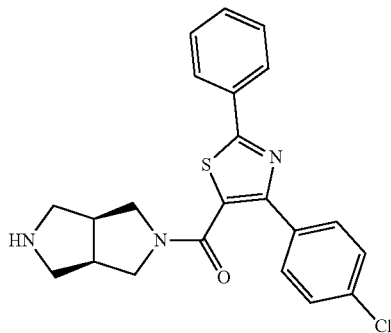 [SMILES: O=C(c1sc(-c2ccccc2)nc1-c1ccc(Cl)cc1)N1C[C@H]2CNC[C@H]2C1]

7. Compound 7: (2-(4-chlorophenyl)-4-phenylthiazol-5-yl)((3aR,6aS)-hexahydropyrrolo[3,4-c]pyrrol-2(1H)-yl)methanone, having the following general structure:

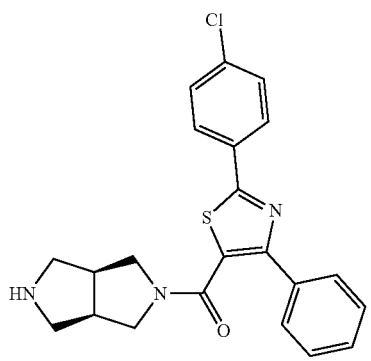 [SMILES: O=C(c1sc(-c2ccc(Cl)cc2)nc1-c1ccccc1)N1C[C@H]2CNC[C@H]2C1]

Figure 5:
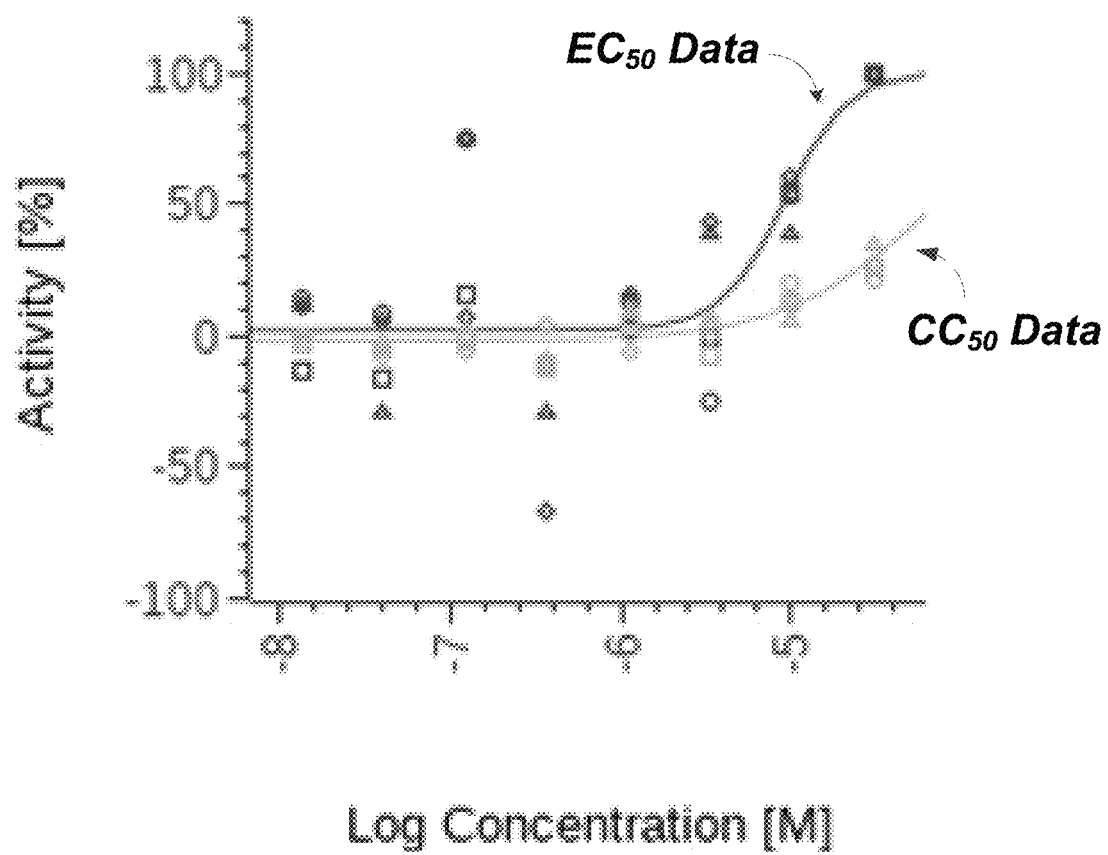
FIG. 5. Dose response curves for Compound 5: (2,4-diphenylthiazol-5-yl)((3aR,6aS)-hexahydropyrrolo[3,4-c]pyrrol-2(1H)-yl)methanone.
Figure 6:
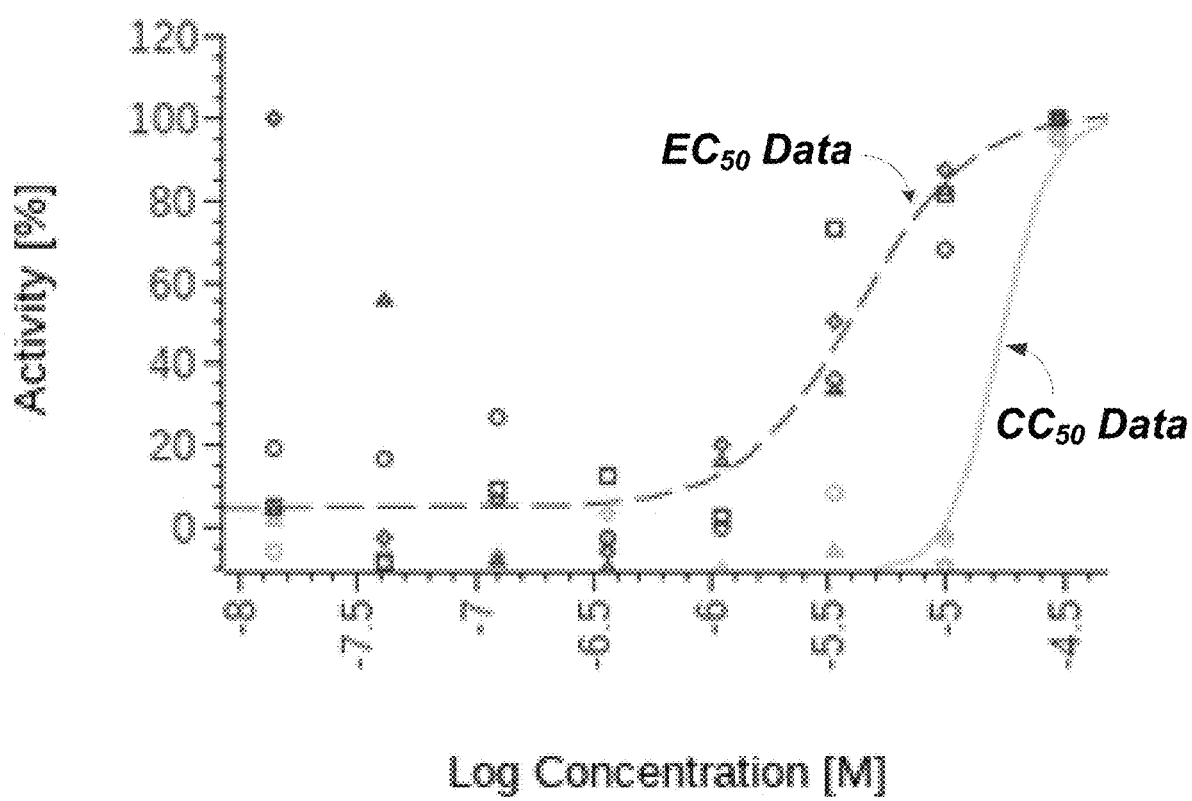
FIG. 6. Dose response curves for Compound 6: (4-(4-chlorophenyl)-2-phenylthiazol-5-yl)((3aR,6aS)-hexahydropyrrolo[3,4-c]pyrrol-2(1H)-yl)methanone.
Figure 7:
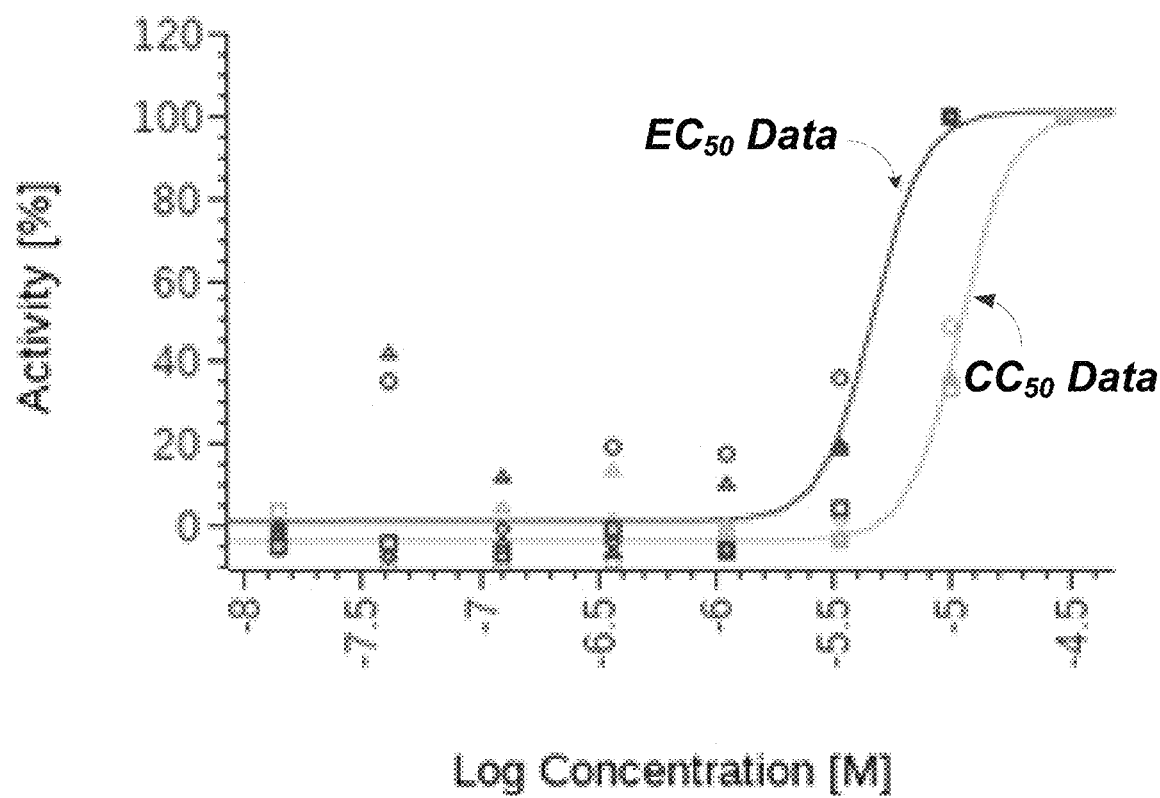
FIG. 7. Dose response curves for Compound 7: (2-(4-chlorophenyl)-4-phenylthiazol-5-yl)((3aR,6aS)-hexahydropyrrolo[3,4-c]pyrrol-2(1H)-yl)methanone.

Table 2 below provides data on potency ($EC_{50}$, $EC_{90}$), cytotoxicity ($CC_{50}$) and SI (selectivity index=$CC_{50}/EC_{50}$) for the above referenced compounds against the SARS-CoV-2 strain. The dose response curves for Compounds 5-7 are provided in FIGS. 5-7, respectively.

TABLE 2

| Compound | $EC_{50}$ (μM) | $EC_{90}$ (μM) | $CC_{50}$ (μM) | SI |
|---|---|---|---|---|
| 5 | 8.3 | 75.00 | 79.7 | 9.6 |
| 6 | 4.2 | 13.29 | 17.1 | >4.0 |
| 7 | 4.7 | 7.96 | 11.0 | 2.3 |

In addition to the above, pharmokinetic (PK) studies have been completed on additional representative compounds of the pyyroloquinazolines noted herein. More specifically, pharmokinetic studies were conducted for Compound 8, 7-(2-(fluorobenzyl)-7H-pyrrolo[3,2-f]quinazoline-1,3-diamine having the following structure:

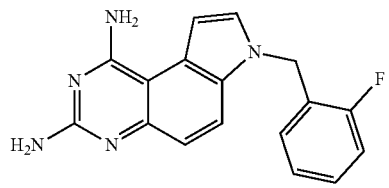 [SMILES: Nc1nc(N)c2c(ccc3c2ccn3Cc2ccccc2F)n1]

Figure 8:
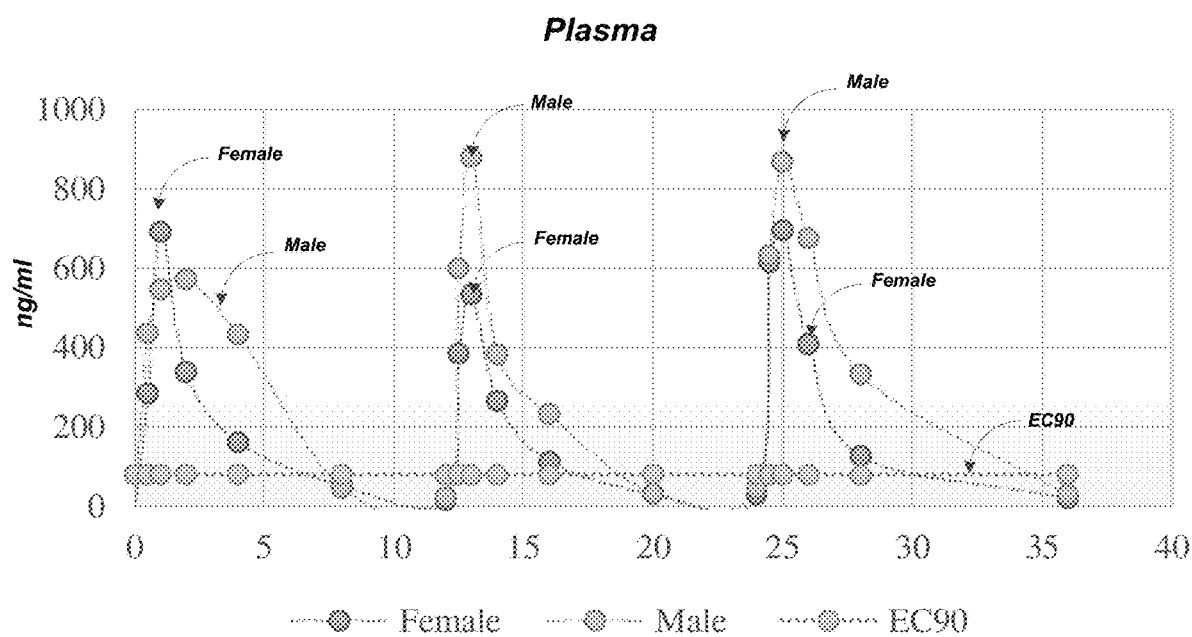
FIG. 8 provides the animal (mice) compound concentration versus time plots in blood plasma for dosing of Compound 8 at 10 mg/kg, subcutaneous, twice-a-day, at time points 0, 0.5, 1, 2, 4, 8, 12 hours post dose up to 36 hours FIG. 9 provides the animal (mice) compound concentration versus time plots also for Compound 8 in the lung at 10 mg/kg, subcutaneous, twice-a-day, at time points 0, 0.5, 1, 2, 4, 8, 12 post dose up to 36 hours.
Figure 9:
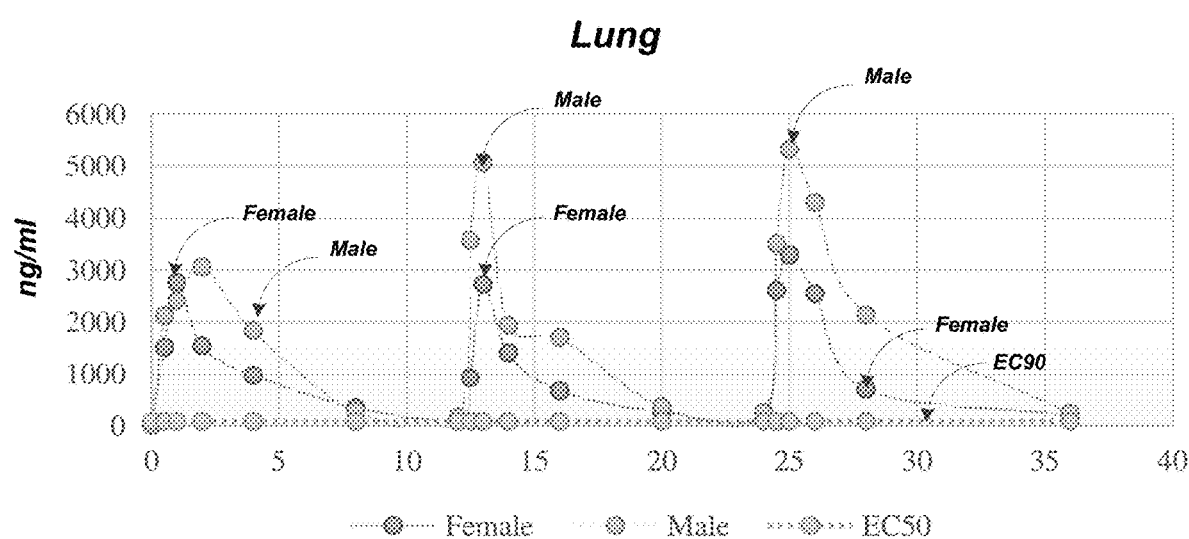

Reference is therefore made to FIG. 8 which provides the animal (mice) compound concentration versus time plots in blood plasma for dosing of Compound 8 at 10 mg/kg, subcutaneous, twice-a-day, at time points 0, 0.5, 1, 2, 4, 8, 12 hours post dose up to 36 hours. FIG. 9 provides the animal (mice) compound concentration versus time plots also for Compound 8 in the lung at 10 mg/kg, subcutaneous, twice-a-day, at time points 0, 0.5, 1, 2, 4, 8, 12 post dose up to 36 hours. Table 3 below provides a summary of this data:

TABLE 3

| PK Studies-Compound 8 | | |
|---|---|---|
| Parameter | Plasma | Lung |
| AUC (ng*hr/ml) | 2137 | 13,046 |
| Half-Life (hr) | 3.1 | 3.74 |
| Cmax (ng/mL) | 675 | 4142 |
| Tmax (ng/mL) | 1.4 | 98.3 |
| Time > EC90(%) | 65 | 98.3 |

AUC-area under the curve.
EC50 = 24.58 ng/mL.
EC90 = 79.90 ng/mL

As may therefore be appreciated from the above, Compound 8 is relatively well-tolerated and achieved concentration levels for a significant percentage of time above EC90 in both blood plasma and the lung.

PK studies were next conducted for Compound 9, 7-(pyridin-3-ylmethyl)-7H-pyrrolo[3,2-f]quinazoline-1,3-diamine, having the following structure:

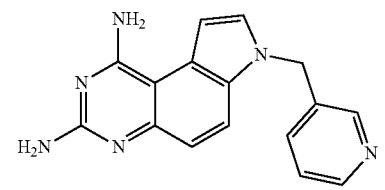 [SMILES: Nc1nc(N)c2c(ccc3c2ccn3Cc2cccnc2)n1]

Figure 10:
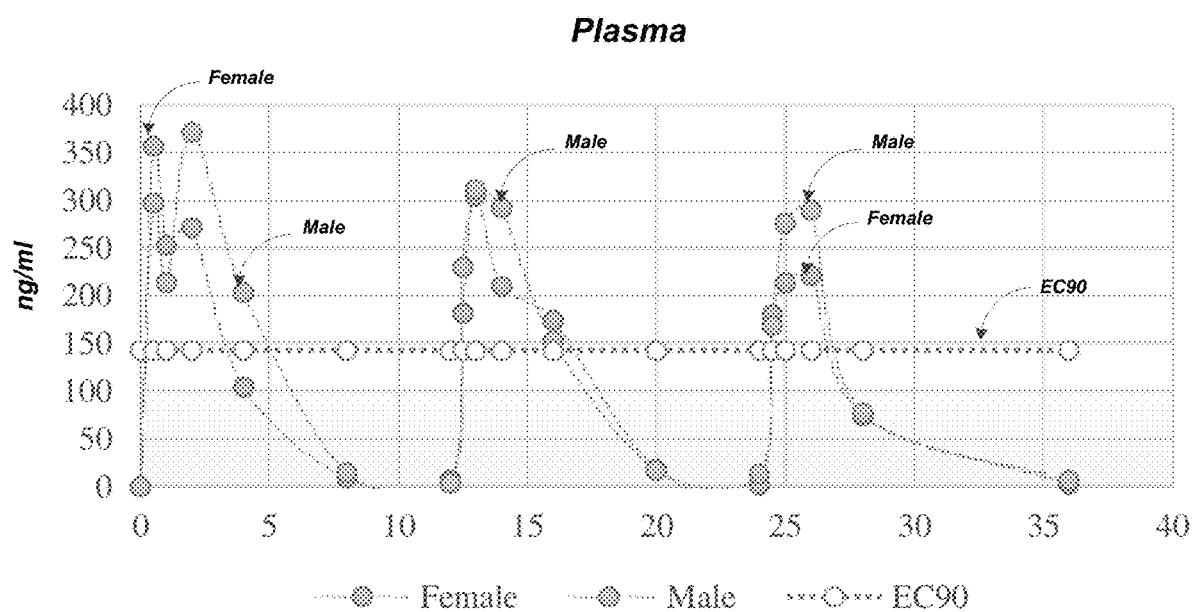
FIG. 10 provides the animal (mice) compound concentration versus time plots in blood plasma for dosing of Compound 9 at 25 mg/kg, subcutaneous, twice-a-day, at time points 0, 0.5, 1, 2, 4, 8, 12 hours post dose up to 36 hours.
Figure 11:
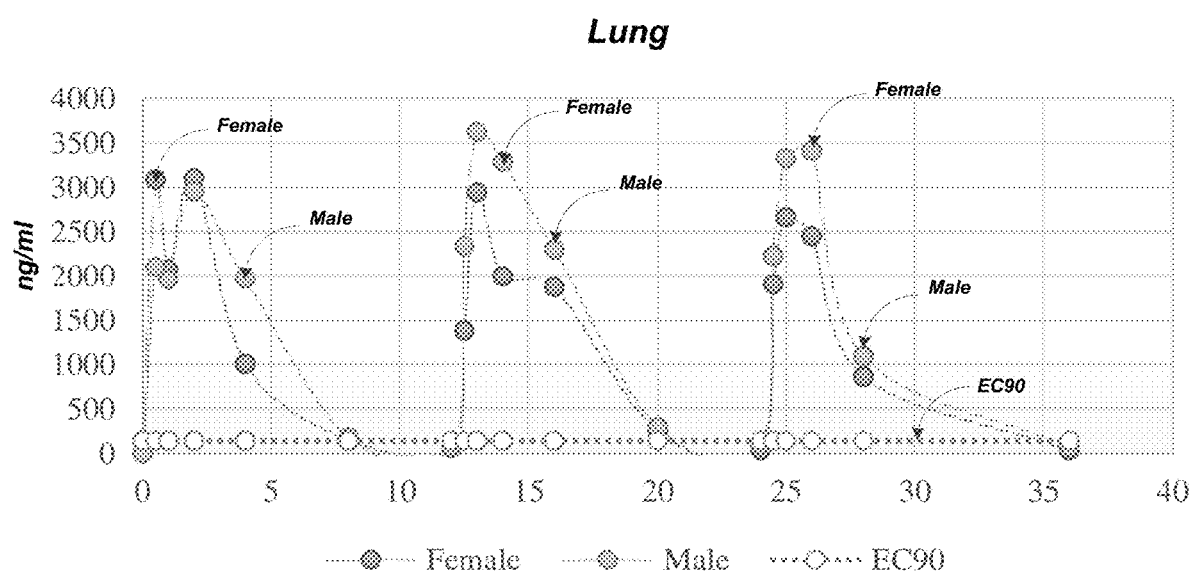
FIG. 11 provides the animal (mice) compound concentration versus time plots also for Compound 9 in the lung at 25 mg/kg, subcutaneous, twice-a-day, at time points 0, 0.5, 1, 2, 4, 8, 12 post dose up to 36 hours.

Reference is therefore made to FIG. 10 which provides the animal (mice) compound concentration versus time plots in blood plasma for dosing of Compound 9 at 25 mg/kg, subcutaneous, twice-a-day, at time points 0, 0.5, 1, 2, 4, 8, 12 hours post dose up to 36 hours. FIG. 11 provides the animal (mice) compound concentration versus time plots also for Compound 9 in the lung at 25 mg/kg, subcutaneous, twice-a-day, at time points 0, 0.5, 1, 2, 4, 8, 12 post dose up to 36 hours. Table 4 below provides a summary of this data:

TABLE 4

| PK Studies-Compound 9 | | |
|---|---|---|
| Parameter | Plasma | Lung |
| AUC (ng*hr/ml) | 1191 | 12,391 |
| Half-Life (hr) | 2.1 | 2.8 |

TABLE 4-continued

PK Studies-Compound 9

| Parameter | Plasma | Lung |
|---|---|---|
| Cmax (ng/mL) | 365 | 3325 |
| Tmax (ng/mL) | 1.6 | 1.9 |
| Time > EC90(%) | 55 | 73 |

AUC-area under the curve.
EC50 = 58.0 ng/mL.
EC90 = 142.2 ng/mL

As may therefore be appreciated from the above, Compound 9 is also relatively well-tolerated and achieved concentration levels for a significant percentage of time above EC90 in both blood plasma and the lung.

PK studies were next conducted for Compound 10, 7-(pyridin-4-ylmethyl)-7H-pyrrolo[3,2-f]quinazoline-1,3-diamine, having the following structure:

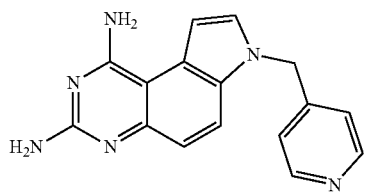 [SMILES: Nc1nc(N)c2c(ccc3c2ccn3Cc2ccncc2)n1]

Figure 12:
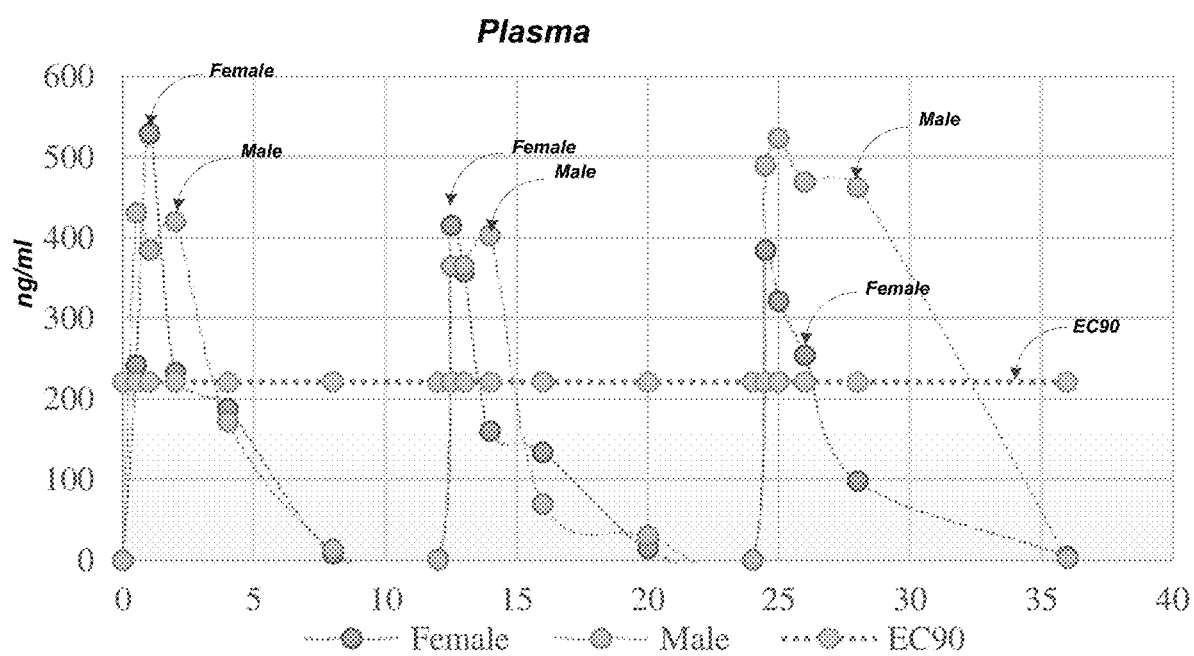
FIG. 12 provides the animal (mice) compound concentration versus time plots in blood plasma for dosing of Compound 10 at 25 mg/kg, subcutaneous, twice-a-day, at time points 0, 0.5, 1, 2, 4, 8, 12 hours post dose up to 36 hours.
Figure 13:
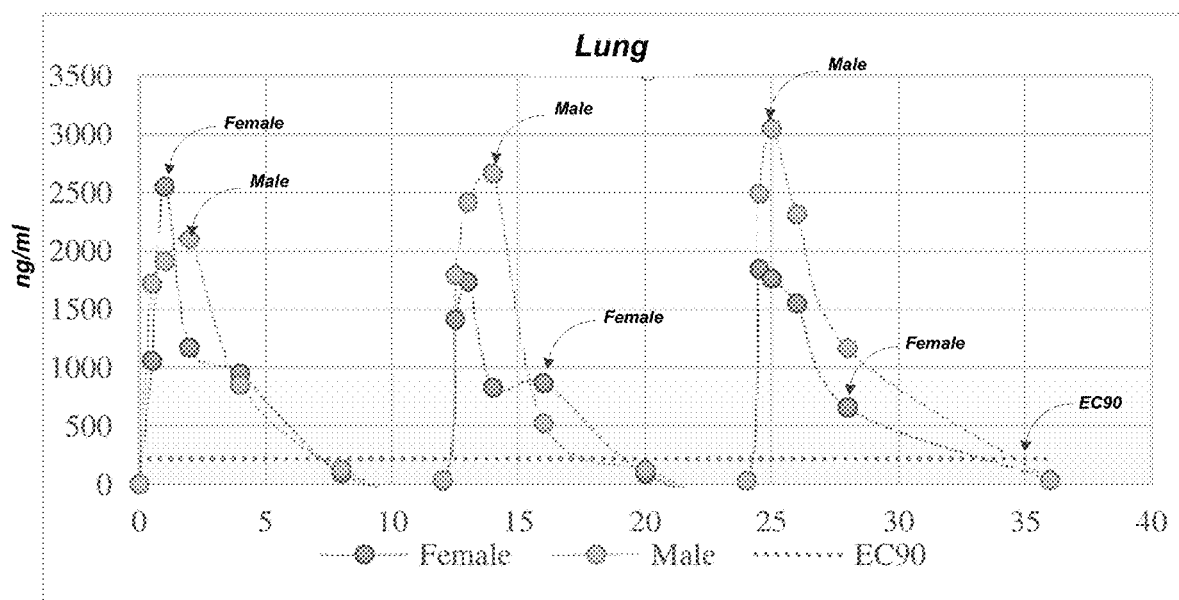
FIG. 13 provides the animal (mice) compound concentration versus time plots also for Compound 10 in the lung at 25 mg/kg, subcutaneous, twice-a-day, at time points 0, 0.5, 1, 2, 4, 8, 12 hours post dose up to 36 hours.

Reference is made to FIG. 12 which provides the animal (mice) compound concentration versus time plots in blood plasma for dosing of Compound 10 at 25 mg/kg, subcutaneous, twice-a-day, at time points 0, 0.5, 1, 2, 4, 8, 12 hours post dose up to 36 hours. FIG. 13 provides the animal (mice) compound concentration versus time plots also for Compound 10 in the lung at 25 mg/kg, subcutaneous, twice-a-day, at time points 0, 0.5, 1, 2, 4, 8, 12 hours post dose up to 36 hours. Table 5 below provides a summary of this data:

TABLE 5

PK Studies-Compound 10

| Parameter | Plasma | Lung |
|---|---|---|
| AUC (ng*hr/ml) | 1596 | 7823 |
| Half-Life (hr) | 2.1 | 2.7 |
| Cmax (ng/mL) | 678 | 2912 |
| Tmax (ng/mL) | 1.2 | 1.2 |
| Time > EC90(%) | 44 | 63 |

AUC-area under the curve.
EC50 = 81.28 ng/mL.
EC90 = 220.64 ng/mL

As may therefore be appreciated from the above, Compound 10 is also relatively well-tolerated and achieved concentration levels for a significant percentage of time above EC90 in both blood plasma and the lung.

PK studies were next conducted for Compound 11, 7-(pyridin-2-ylmethyl)-7H-pyrrolo[3,2-f]quinazoline-1,3-diamine, having the following structure

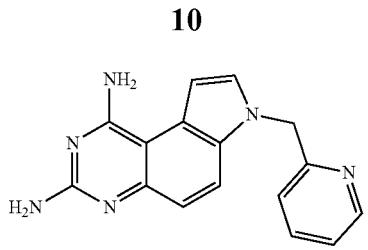

Figure 14:
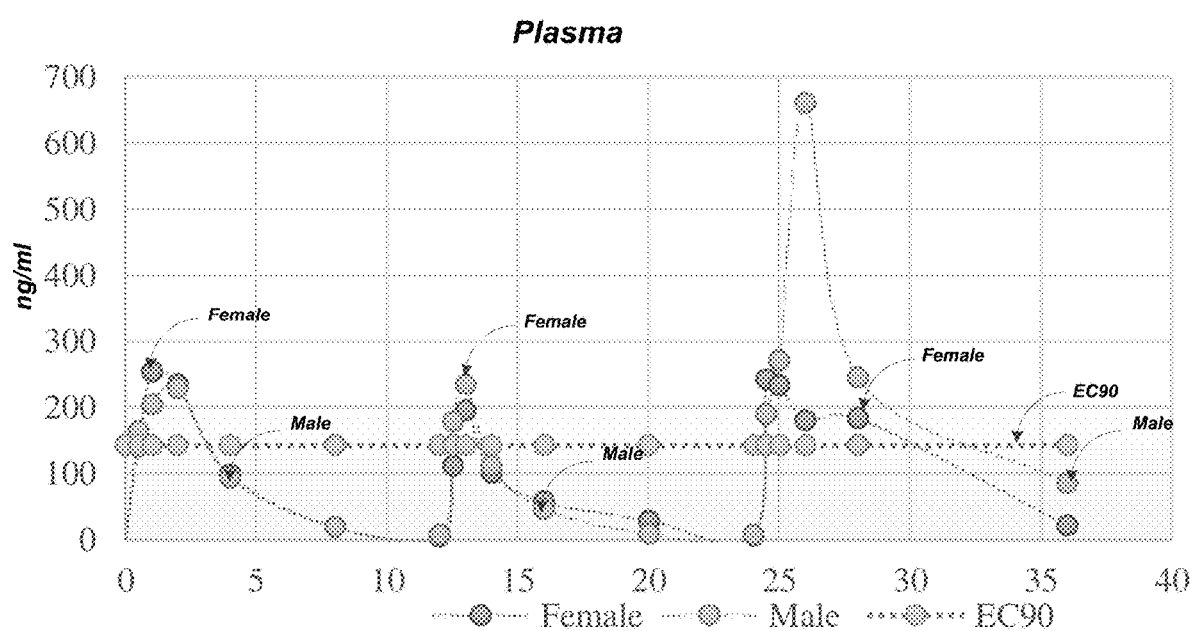
FIG. 14 provides the animal (mice) compound concentration versus time plots in blood plasma for dosing of Compound 11 at 25 mg/kg, subcutaneous, twice-a-day, at time points 0, 0.5, 1, 2, 4, 8, 12 hours post dose up to 36 hours.
Figure 15:
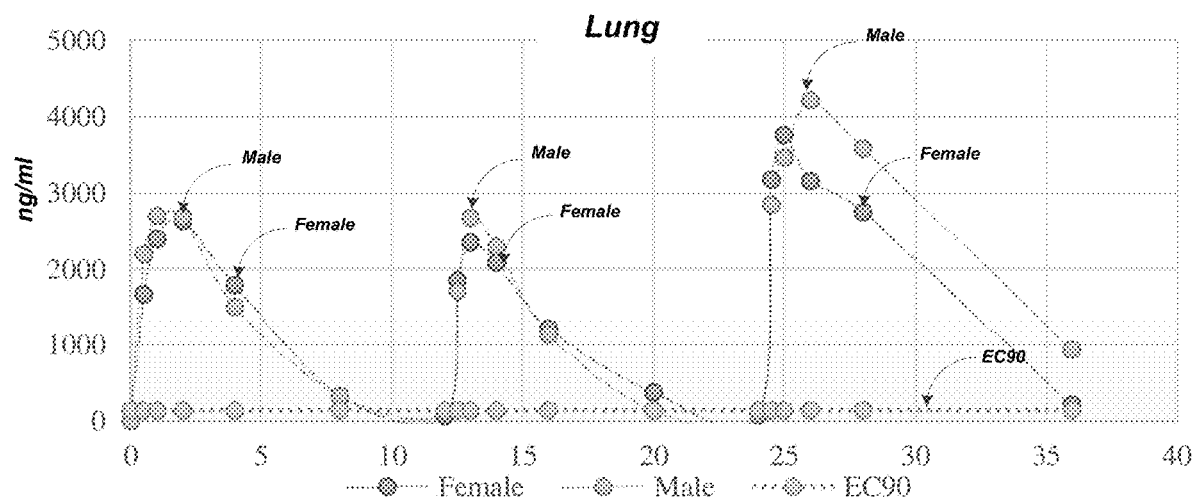
FIG. 15 provides the animal (mice) compound concentration versus time plots also for Compound 11 in the lung at 25 mg/kg, subcutaneous, twice-a-day, at time points 0, 0.5, 1, 2, 4, 8, 12 hours post dose up to 36 hours.

Reference is made to FIG. 14 which provides the animal (mice) compound concentration versus time plots in blood plasma for dosing of Compound 11 at 25 mg/kg, subcutaneous, twice-a-day, at time points 0, 0.5, 1, 2, 4, 8, 12 hours post dose up to 36 hours. FIG. 15 provides the animal (mice) compound concentration versus time plots also for Compound 11 in the lung at 25 mg/kg, subcutaneous, twice-a-day, at time points 0, 0.5, 1, 2, 4, 8, 12 hours post does up to 36 hours. Table 6 below provides a summary of this data:

TABLE 6

PK Studies-Compound 11

| Parameter | Plasma | Lung |
|---|---|---|
| AUC (ng*hr/ml) | 1167 | 14,634 |
| Half-Life (hr) | 2.6 | 3.3 |
| Cmax (ng/mL) | 348 | 3274 |
| Tmax (ng/mL) | 1.6 | 1.28 |
| Time > EC90(%) | 45 | 85 |

AUC-area under the curve.
EC50 = 43.54 ng/mL.
EC90 = 142.25 ng/mL

As may therefore be appreciated from the above, Compound 11 is also relatively well-tolerated and achieved concentration levels for a significant percentage of time above EC90 in both blood plasma and the lung.

PK studies were next conducted for Compound 12, 7-(cyclohexylmethyl)-7H-pyrrolo[3,2-f]quinazoline-1,3-diamine, having the following general structure:

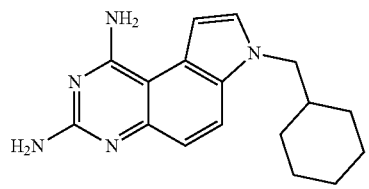 [SMILES: Nc1nc(N)c2c(ccc3c2ccn3CC2CCCCC2)n1]

Figure 16:
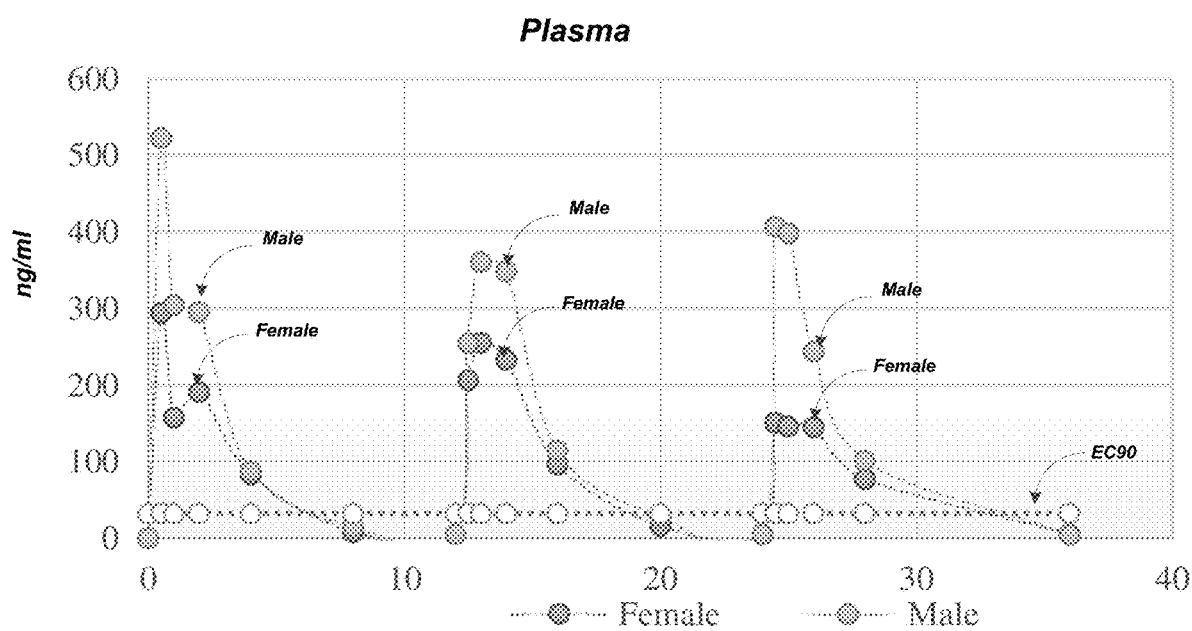
FIG. 16 provides the animal (mice) compound concentration versus time plots in blood plasma for dosing of Compound 12 at 10 mg/kg, subcutaneous, twice-a-day, at time points 0, 0.5, 1, 2, 4, 8, 12 hours post dose up to 36 hours.
Figure 17:
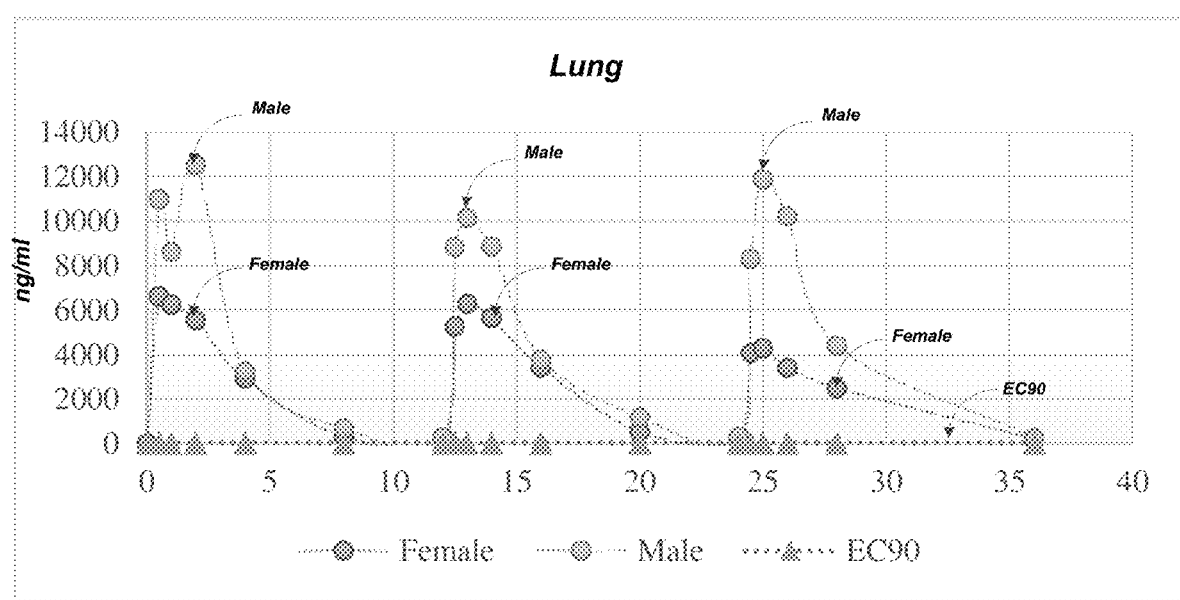
FIG. 17 provides the animal (mice) compound concentration versus time plots also for Compound 12 in the lung at 10 mg/kg, subcutaneous, twice-a-day, at time points 0, 0.5, 1, 2, 4, 8, 12 hours post dose up to 36 hours.

Reference is made to FIG. 16 which provides the animal (mice) compound concentration versus time plots in blood plasma for dosing of Compound 12 at 10 mg/kg, subcutaneous, twice-a-day, at time points 0, 0.5, 1, 2, 4, 8, 12 hours post dose up to 36 hours. FIG. 17 provides the animal (mice) compound concentration versus time plots also for Compound 12 in the lung at 10 mg/kg, subcutaneous, twice-a-day, at time points 0, 0.5, 1, 2, 4, 8, 12 hours post dose up to 36 hours. Table 7 below provides a summary of this data:

TABLE 6

PK Studies-Compound 12

| Parameter | Plasma | Lung |
|---|---|---|
| AUC (ng*hr/ml) | 968 | 34,100 |
| Half-Life (hr) | 4.2 | 3.1 |

TABLE 6-continued

PK Studies-Compound 12

| Parameter | Plasma | Lung |
| --- | --- | --- |
| Cmax (ng/mL) | 348 | 10,107 |
| Tmax (ng/mL) | 1.4 | 1.4 |
| Time > EC90(%) | 64 | 100 |

AUC-area under the curve.
EC50 = 17.72 ng/mL.
EC90 = 32.49 ng/mL

As may therefore be appreciated from the above, Compound 12 is also relatively well-tolerated and achieved concentration levels for a significant percentage of time above EC90 in both blood plasma and the lung.

Table 7 below provides data on potency ($EC_{50}$, $EC_{90}$), cytotoxicity ($CC_{50}$) and SI (selectivity index=$CC_{50}/EC_{50}$) for Compounds 8-12 against the SARS-CoV-2 strain.

TABLE 7

| Compound | $EC_{50}$ (µM) | $EC_{90}$ (µM) | $CC_{50}$ (µM) | SI |
| --- | --- | --- | --- | --- |
| 8 | 0.05 ± 0.031 | 0.16 ± 0.142 | 4.89 ± 4.7 | 98 |
| 9 | 0.16 ± 0.061 | 0.36 ± 0.193 | >30 | >187 |
| 10 | 0.08 ± 0.012 | 0.24 ± 0.11 | >30 | >375 |
| 11 | 0.12 ± 0.05 | 0.36 ± 0.23 | 15.46 ± 10.6 | 128 |
| 12 | 0.12 ± 0.087 | 0.32 ± 0.32 | 4.91 ± 0.2 | 41 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for treatment of COVID-19 caused by SARS-COV-1, SARS-CoV-2 (Covid-19) and MERS-CoV, and variants within each, in a mammalian subject in need therefore, comprising administering to the subject an effective amount of a pyrroloquinazoline of the following formulae:

wherein
X₁ and X₂ are CH and joined together by a double bond;
Y is independently C;
Z is $CH_2$;
$R_1$ is 2-trifluorophenyl, 2-methylphenyl, 4-nitrophenyl, ethylene, 2-fluorophenyl, pyridine-3-yl, pyridine-2-yl, pyridine-4-yl or cyclohexyl;
$R_2$ is H or methyl;
$R_3$ is H;
$R_4$ and $R_5$ are independently amino groups;
or a pharmaceutically acceptable salt thereof, optionally in a pharmaceutically acceptable carrier.

2. The method of claim 1 wherein said pyrroloquinazoline comprises 7-(2-(trifluoromethyl)benzyl)-7H-pyrrolo[3,2-f]quinazoline-1,3-diamine.

3. The method of claim 1 wherein said pyrroloquinazoline comprises 7-(2-methylbenzyl)-7H-pyrrolo[3,2-f]quinazoline-1,3-diamine.

4. The method of claim 1 wherein said pyrroloquinazoline comprises 4-((1,3-diamino-8-methyl-7H-pyrrolo [3,2-f]quinazolin-7-yl)methyl)benzonitrile.

5. The method of claim 1 wherein said pyrroloquinazoline comprises 7-allyl-7H-pyrrolo[3,2-fiquinazoline-1,3-diamine.

6. The method of claim 1 wherein said pyrroloquinazoline comprises 7-(2-(fluorobenzyl)-7H-pyrrolo[3,2-f]quinazoline-1,3-diamine.

7. The method of claim 1 wherein said pyrroloquinazoline comprises 7-(pyridin-3-ylmethyl)-7H-pyrrolo [3,2-f]quinazoline-1,3-diamine.

8. The method of claim 1 wherein said pyrroloquinazoline comprises 7-(pyridin-4-ylmethyl)-7H-pyrrolo[3,2-fiquinazoline-1,3-diamine.

9. The method of claim 1 wherein said pyrroloquinazoline comprises 7-(pyridin-2-ylmethyl)-7H-pyrrolo[3,2-fiquinazoline-1,3-diamine.

10. The method of claim 1 wherein said pyrroloquinazoline comprises 7-(cyclohexylmethyl)-7H-pyrrolo[3,2-fiquinazoline-1,3-diamine.

* * * * *